(12) United States Patent
Wan et al.

(10) Patent No.: US 11,484,598 B1
(45) Date of Patent: Nov. 1, 2022

(54) PLEUROMULIN RHEIN ESTER WITH ANTI-DRUG RESISTANT BACTERIA ACTIVITY AND A METHOD OF PREPARING THE SAME

(71) Applicants: Jia Wan, Xi'an (CN); Chunchun Kong, Xi'an (CN); Jingyi Li, Xi'an (CN); Qianqian Zhao, Xi'an (CN); Dan Yang, Xi'an (CN)

(72) Inventors: Jia Wan, Xi'an (CN); Chunchun Kong, Xi'an (CN); Jingyi Li, Xi'an (CN); Qianqian Zhao, Xi'an (CN); Dan Yang, Xi'an (CN)

(73) Assignee: XI'AN KANGYUANSHENG BIOMEDICAL TECHNOLOGY CO., LTD., Xi'an (CN)

( * ) Notice: Subject to any disclaimer, the term of this patent is extended or adjusted under 35 U.S.C. 154(b) by 0 days.

(21) Appl. No.: 17/460,267

(22) Filed: Aug. 29, 2021

(30) Foreign Application Priority Data

Apr. 13, 2021 (CN) .......................... 202110391549.8

(51) Int. Cl.
*A61K 47/55* (2017.01)
*C07C 69/94* (2006.01)
*C07C 67/14* (2006.01)

(52) U.S. Cl.
CPC ............ *A61K 47/552* (2017.08); *C07C 67/14* (2013.01); *C07C 69/94* (2013.01); *C07C 2603/24* (2017.05); *C07C 2603/82* (2017.05)

(58) Field of Classification Search
CPC ...... A61K 47/552; C07C 67/14; C07C 69/94; C07C 2603/24; C07C 2603/82
USPC .......................................................... 560/53
See application file for complete search history.

(56) References Cited

PUBLICATIONS

Deng et al., Arch. Pharm. Chem. Life Sci, year 2018, 352 pp. 1-8.*

* cited by examiner

*Primary Examiner* — Ana Z Muresan

(57) ABSTRACT

A compound with anti-drug resistant bacteria activity having the following formula

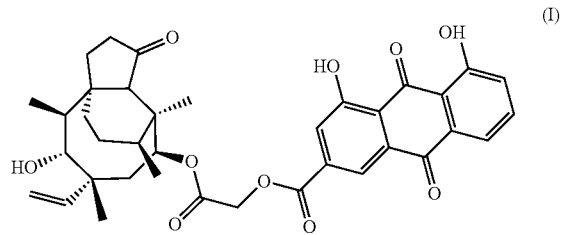

(I)

is disclosed. A method of preparing the compound of formula (I) is also disclosed.

10 Claims, 2 Drawing Sheets positive 128 64 32 16 8 4 2 1 negative positive 128 64 32 16 8 4 2 1 negative

PLEUROMULIN RHEIN ESTER WITH ANTI-DRUG RESISTANT BACTERIA ACTIVITY AND A METHOD OF PREPARING THE SAME

This application claims priority to Chinese Patent Application No. 202110391549.8, filed on Apr. 13, 2021, which is incorporated by reference for all purposes as if fully set forth herein.

FIELD OF THE INVENTION

The present invention relates to the field of medicinal chemistry, and in particular, to a pleuromulin rhein ester with anti-drug resistant bacteria activity and a method of preparing the same.

BACKGROUND OF THE INVENTION

With the widespread use of antibacterial drugs and the increase in various invasive operations, the spectrum of clinical infection pathogens continues to change, and bacterial resistance continues to increase. The infection rate of multidrug-resistant bacteria (MDROs) and the mortality of patients have been increasing year by year. MDROs include methicillin-resistant *Staphylococcus aureus* (MRSA), methicillin-resistant coagulase-negative *Staphylococcus* (MRCNS), ESBLs producing *Escherichia coli* and *Klebsiella pneumoniae*, and carbapenem-resistant *Enterobacter* (CRE), multi-drug-resistant *Enterobacter*, multi-drug-resistant *Acinetobacter baumannii* (MDRAB), multi-drug-resistant *Pseudomonas aeruginosa* (MDRPA), multi-drug-resistant *Enterococcus*, multi-drug-resistant *Streptococcus pneumoniae*, a total of 10 types. *Acinetobacter baumannii* and *Pseudomonas aeruginosa* are widely distributed in the medical environment and have a long survival time. They can form a biofilm on the surface of various medical devices and supplies. It is difficult to eliminate and easy to colonize the natural cavity mucosa of patients. The treatment caused serious difficulties. Nowadays, the problem of bacterial resistance is becoming more and more serious. It is particularly important to find compounds with good antibacterial activity, unique antibacterial mechanism, not easy to cross-resistance with other drugs, and new structures.

Pleuromulin is a diterpene compound produced by the higher fungi of the basidiomycete *Pleurotus pleurotusmutilis* and *Pleurotus passeckeranius* strains through deep culture. Pleuromulin and its derivatives have unique effects on many gram-positive bacteria, some gram-negative refractory bacteria and mycoplasma infections. This class of antibiotics achieves antibacterial activity by selectively inhibiting protein synthesis. This method is different from the antibacterial mechanism of other antibiotics that inhibit protein synthesis. It is a unique mechanism that combines with prokaryotic ribosomes. Through the clinical use of truncated Pleurotin, it is proved that the emergence of bacterial specific target resistance is very slow, and cross resistance to mupirocin, β-lactam, macrolide antibiotics or quinolones has not been found.

Rhein is a lipophilic anthraquinone compound widely found in Chinese herbal medicines such as rhubarb, cassia seed, fleece-flower root, aloe, etc. It has anti-tumor activity, antibacterial activity, immunosuppressive effect, diuretic effect, laxative effect, and anti-inflammatory effect. It also has the effect of treating diabetes and kidney disease. Previous studies have shown that rhein has good antibacterial activity against *Staphylococcus aureus*, *Helicobacter pylori*, *Streptococcus*, Diphtheria, *Bacillus subtilis*, *Bacillus anthracis*, etc. Its antibacterial mechanism may be related to rhein inhibiting the biosynthesis of bacterial DNA and RNA, hindering the electron transmission of the mitochondrial respiratory chain, and preventing the transcription of genes responsible for bacterial anaerobic respiration and fermentation.

In the present invention, pleuromulin is modified by the rhein structure to obtain a pleuromulin rhein ester. The preliminary antibacterial activity experiment shows the compound has excellent antibacterial activity and has high medical research and application value in the treatment of infectious diseases caused by multidrug resistant bacteria.

SUMMARY OF THE INVENTION

In one embodiment, the present invention provides a pleuromulin rhein ester, which can be used as a new type of antibacterial drug for treating infectious diseases caused by multi-drug resistant bacteria infection. The structural formula of the compound of the present invention is as shown in Formula I.

In another embodiment, the present invention provides a method of preparing the compound of formula (I). The method includes reacting the compound of formula (II) with the compound of formula (III) in organic solvent to obtain the compound of formula (I):

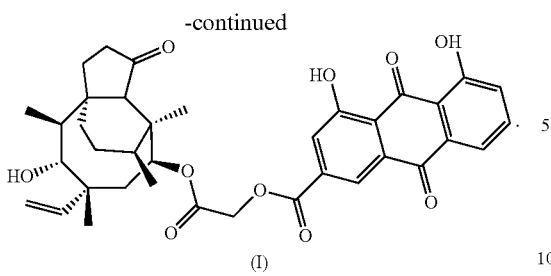

(I)

In another embodiment, the reaction of the compound of formula (II) with the compound of formula (III) includes the following steps: placing the compound of formula (II) and the compound of formula (III), in a molar ratio of 1:1 to 1:1.3, in a reactor; adding an organic solvent and a catalytic amount of triethylamine under nitrogen atmosphere to obtain a reaction mixture; heating the reaction mixture at 20-70° C. for 3-6 hours; extracting the concentrated solution with ethyl acetate to obtain a crude product; and purifying the crude product on a silica gel fresh chromatography column with dichloromethane and ethyl acetate as an eluent to obtain the compound of formula (I).

In another embodiment, the organic solvent is toluene, dichloromethane or N,N-Dimethylformamide.

In another embodiment, the organic solvent is dichloromethane.

In another embodiment, the molar ratio of the compound of formula (II) and the compound of formula (III) is 1:1.1.

In another embodiment, the reaction mixture is heated at 25° C.

In another embodiment, the reaction mixture is heated for 5 hours.

In another embodiment, the eluent is dichloromethane: ethyl acetate=2:1.

In another embodiment, the compound is effective against multi-drug-resistant *Staphylococcus aureus*, multi-drug-resistant *Pseudomonas aeruginosa* and multi-drug-resistant *Acinetobacter baumannii*.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
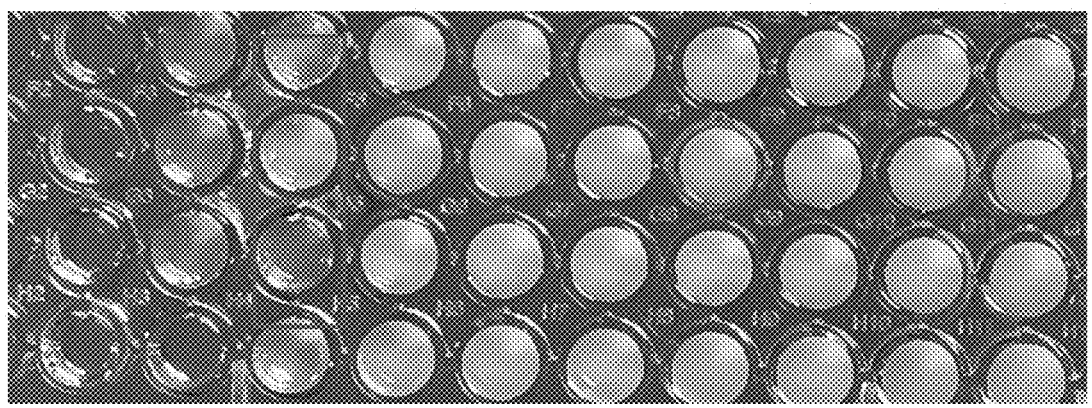
FIG. 1 shows the in vitro antibacterial activity of the pleuromulin rhein ester against drug-resistant bacteria MARS 18-575.

Reference will now be made in detail to embodiments of the present invention, example of which is illustrated in the accompanying drawings. The following examples illustrate the present invention, but the present invention is not limited to the following examples.

Example 1

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate (pleuromulin rhein ester)

A certain amount of rhein and oxalyl chloride were added to dichloromethane in a reactor under nitrogen atmosphere. DMF (dimethylformamide) was added as a catalyst, The reaction was carried out at 25° C. for 2 hours to obtain a rhein derivative (acid chloride), the compound of formula (III).

In a 200 mL three-necked flask, 246.0 mg (0.65 mmol) of pleuromulin (compound of formula (II)) and 6.1 mg (0.06 mmol) triethylamine were dissolved in 50 mL of dichloromethane under nitrogen atmosphere. 214.4 mg (0.71 mmol) of the rhein derivative was dissolved in 20 mL of dichloromethane, and slowly added dropwise to the reaction mixture by a separatory funnel. After the completion of the dropwise addition, the reaction was carried out at 25° C. for 5 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=2:1 as eluent, and the eluent was concentrated under reduced pressure and dried to obtain 302.2 mg of the pleuromulin rhein ester, a total yield of 73.78%.

$^1$H-NMR (400 MHz, chloroform-d) δ (ppm): 12.06 (1H, d), 8.51 (1H, s), 8.03 (1H, s), 7.92 (1H, d), 7.80 (1H, d), 7.39 (1H, d), 6.51 (1H, t), 5.89 (1H, d), 5.41 (2H, s), 5.24 (1H, d), 4.92 (1H, d), 4.15 (1H, t), 4.07 (1H, s), 3.42 (1H, d), 2.26 (1H, d), 2.17-2.08 (4H, t), 1.80-1.28 (12H, t), 0.85 (3H, s), 0.78 (3H, d); $^{13}$C-NMR (100 MHz, chloroform-d) δ (ppm): 216.7, 172.1, 162.9, 138.9, 138.7, 125.6, 120.4, 117.3, 74.6, 69.9, 58.1, 45.4, 44.8, 44.0, 41.9, 36.6, 36.1, 34.4, 30.4, 26.8, 26.4, 24.8, 16.6, 14.8, 11.5.

Example 2

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of N,N-dimethylformamide under nitrogen atmosphere. 214.4 mg (0.71 mmol) of the rhein derivative was dissolved in 20 mL of N,N-dimethylformamide, and slowly added dropwise to the reaction mixture by a separatory funnel. After the completion of the dropwise addition, the reaction was carried out at 25° C. for 4 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=2:1 as eluent, and the eluent was concentrated under reduced pressure and dried to obtain 256.2 mg of the pleuromulin rhein ester, a total yield of 62.55%.

Example 3

Preparation of Compound 2-(((3aR,4R,5S,6S,8R, 9R)-5-hydroxy-4,6,9-trimethyl-1-oxo-6-vinyldecahydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of toluene under nitrogen atmosphere. 214.4 mg (0.71 mmol) of the rhein derivative was dissolved in 20 mL of toluene, and slowly added dropwise to the reaction mixture by a separatory funnel. After the completion of the dropwise addition, the reaction was carried out at 30° C. for 6 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=2:1 as eluent, and the eluent was concentrated under reduced pressure and dried to obtain 268.0 mg of the pleuromulin rhein ester, a total yield of 65.43%.

Example 4

Preparation of Compound 2-(((3aR,4R,5S,6S,8R, 9R)-5-hydroxy-4,6,9-trimethyl-1-oxo-6-vinyldecahydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of dichloromethane under nitrogen atmosphere. 214.4 mg (0.71 mmol) of the rhein derivative was dissolved in 20 mL of dichloromethane, and slowly added dropwise to the reaction mixture by a separatory funnel. After the completion of the dropwise addition, the reaction was carried out at 30° C. for 6 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=2:1 as eluent, and the eluent was concentrated under reduced pressure and dried to obtain 275.1 mg of the pleuromulin rhein ester, a total yield of 67.15%.

Example 5

Preparation of Compound 2-(((3aR,4R,5S,6S,8R, 9R)-5-hydroxy-4,6,9-trimethyl-1-oxo-6-vinyldecahydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of N,N-dimethylformamide under nitrogen atmosphere. 235.6 mg (0.78 mmol) of the rhein derivative was dissolved in 20 mL of N,N-dimethylformamide, and slowly added dropwise to the reaction mixture by a separatory funnel. After the completion of the dropwise addition, the reaction was carried out at 25° C. for 4 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=2:1 as eluent, and the eluent was concentrated under reduced pressure and dried to obtain 260.4 mg of the pleuromulin rhein ester, a total yield of 63.57%.

Example 6

Preparation of Compound 2-(((3aR,4R,5S,6S,8R, 9R)-5-hydroxy-4,6,9-trimethyl-1-oxo-6-vinyldecahydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of dichloromethane under nitrogen atmosphere. 256.7 mg (0.85 mmol) of the rhein derivative was dissolved in 20 mL of dichloromethane, and slowly added dropwise to the reaction mixture by a separatory funnel. After the completion of the dropwise addition, the reaction was carried out at 25° C. for 3 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=1:1 as eluent, and the eluent was concentrated under reduced pressure and dried to obtain 269.5 mg of the pleuromulin rhein ester, a total yield of 65.78%.

Example 7

Preparation of Compound 2-(((3aR,4R,5S,6S,8R, 9R)-5-hydroxy-4,6,9-trimethyl-1-oxo-6-vinyldecahydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of toluene under nitrogen atmosphere. 217.4 mg (0.72 mmol) of the rhein derivative was dissolved in 20 mL of toluene, and slowly added dropwise to the reaction mixture by a separatory funnel. After the completion of the dropwise addition, the reaction was carried out at 60° C. for 3 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=3:1 as eluent, and the eluent was concentrated under reduced pressure and dried to obtain 254.5 mg of the pleuromulin rhein ester, a total yield of 61.63%.

Example 8

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of dichloromethane under nitrogen atmosphere. 235.6 mg (0.78 mmol) of the rhein derivative was dissolved in 20 mL of dichloromethane, and slowly added dropwise to the reaction mixture by a separatory funnel. After the completion of the dropwise addition, the reaction was carried out at 30° C. for 5 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=1:1 as eluent, and the eluent was concentrated under reduced pressure and dried to obtain 251.4 mg of the pleuromulin rhein ester, a total yield of 61.36%.

Example 9

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of toluene under nitrogen atmosphere. 235.6 mg (0.78 mmol) of the rhein derivative was dissolved in 20 mL of toluene, and slowly added dropwise to the reaction mixture by a separatory funnel. After the completion of the dropwise addition, the reaction was carried out at 65° C. for 3 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=3:1 as eluent, and the eluent was concentrated under reduced pressure and dried to obtain 261.7 mg of the pleuromulin rhein ester, a total yield of 63.88%.

Example 10

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of toluene under nitrogen atmosphere. 196.3 mg (0.65 mmol) of the rhein derivative was dissolved in 20 mL of toluene, and slowly added dropwise to the reaction mixture by a separatory funnel. After the completion of the dropwise addition, the reaction was carried out at 50° C. for 5 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=3:1 as eluent, and the eluent was concentrated under reduced pressure and dried to obtain 263.9 mg of the pleuromulin rhein ester, a total yield of 64.41%.

Example 11

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of dichloromethane under nitrogen atmosphere. 253.7 mg (0.84 mmol) of the rhein derivative was dissolved in 20 mL of dichloromethane, and slowly added dropwise to the reaction mixture by a separatory funnel. After the completion of the dropwise addition, the reaction was carried out at 40° C. for 4 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=1:1 as eluent, and the eluent was concentrated under reduced pressure and dried to obtain 268.9 mg of the pleuromulin rhein ester, a total yield of 65.63%.

Example 12

Preparation of Compound 2-(((3aR,4R,5S,6S,8R, 9R)-5-hydroxy-4,6,9-trimethyl-1-oxo-6-vinyldeca-hydro-3a,9-propanocyclopenta[8]annulen-8-yl)oxy)-2-oxoethyl4,5-dihydroxy-9,10-dioxo-9,10-dihydroanthracene-2-carboxylate In a 200 mL three-necked flask, 246.0 mg (0.65 mmol) of pleuromulin and 6.1 mg (0.06 mmol) triethylamine were dissolved in 50 mL of dichloromethane under nitrogen atmosphere. 196.3 mg (0.65 mmol) of the rhein derivative was dissolved in 20 mL of dichloromethane, and slowly added dropwise to the reaction mixture by a separatory funnel. After the completion of the dropwise addition, the reaction was carried out at 20° C. for 5 hours. Thin layer chromatography was used to track the reaction to completion, heating was stopped, and then the protective device was removed. The reaction solution was concentrated, washed with water, extracted with ethyl acetate, and concentrated and dried to obtain a pleuromulin rhein ester crude product. The crude product was further purified by silica gel column chromatography, with dichloromethane/ethyl acetate=2:1 as eluent, and the eluent was concentrated under reduced pressure and dried to obtain 288.9 mg of the pleuromulin rhein ester, a total yield of 70.53%.

Example 13

Antibacterial Activity Test of the Compounds of the Invention

The minimal inhibitory concentration (MIC) of the compounds as determined by microbroth dilution method was measured with ceftazidime and vancomycin as positive control.

The experimental strains included drug-resistant gram-positive bacteria: methicillin-resistant *Staphylococcus aureus* MRSA 18-575; drug-resistant gram-negative bacteria: multi-drug-resistant *Pseudomonas aeruginosa* MDR-PA 18-126, 18-756, Carbapenem-resistant *Acinetobacter baumannii* CR-AB 18-184, 18-560. The experimental strains were all donated by Huashan Hospital Affiliated to Fudan University (Fudan University Antibiotic Research Institute), and used after being identified by conventional methods.

Preparation of Test Strains:

Preparation of MHB medium: 20.0 g NMB medium was added to 1 L distilled water, boiled until completely dissolved, packed in conical bottles and sterilized at 121° C. for 15 min.

The experimental strain was cultured to the logarithmic growth phase: under aseptic condition, the experimental strain was inoculated into 100 mL NMB medium and incubated in a constant temperature and humidity incubator at 37° C. for 20-22 hours.

Preparation of storage solution: weighing the sample to be tested, dissolving it with 1% DMSO solution, preparing a storage solution with a concentration of 2560 µg/mL, weighing a positive reference substance, dissolving it with aseptic distilled water, and configuring a stock solution with a concentration of 2560 µg/mL.

Preparation of bacterial suspension: under aseptic condition, the experimental strains cultured to logarithmic growth phase were adjusted to 0.5 MCF turbidity standard with MHB medium and diluted according to 1:10, and the bacterial suspension with concentration of $10^6$ CFU/mL was prepared for standby.

Stock solution dilution and inoculation of experimental strains: under aseptic conditions, diluting the stock solution to a solution of 256 µg/mL, taking a sterile 96-well plate, adding 100 µL of MHB medium to each well except for the first and second wells; adding 100 µL of positive control solution to the first well, and adding 100 µL of compound sample solution to the second and third wells; mixing the sample solution in the 3 wells with the medium, and then pipetting 100 µL to the 4th well, and then pipetting 100 µL to the 5th well after mixing, and then diluting to the 9th well in a series of times, and drawing 100 µL from the 9th well and discard, the 10th well is a growth control without drugs; then, adding 100 µL of the above-prepared bacterial suspension to each well to make the final bacterial concentration of each well $5\times10^5$ CFU/mL; the positive control concentration was 128 µg/mL, the concentrations of the sample solution were 128, 64, 32, 16, 8, 4, 2, 1 µg/mL.

Incubation: covering the 96-well plate inoculated with the experimental strains, and incubating in a constant temperature and humidity box at 37° C. for 20-22 hours.

Interpretation of the MIC endpoint: the concentration that can completely inhibit the growth of bacteria in a 96-well plate under a black background is the lowest inhibitory concentration of the sample against the bacteria.

Figure 2:
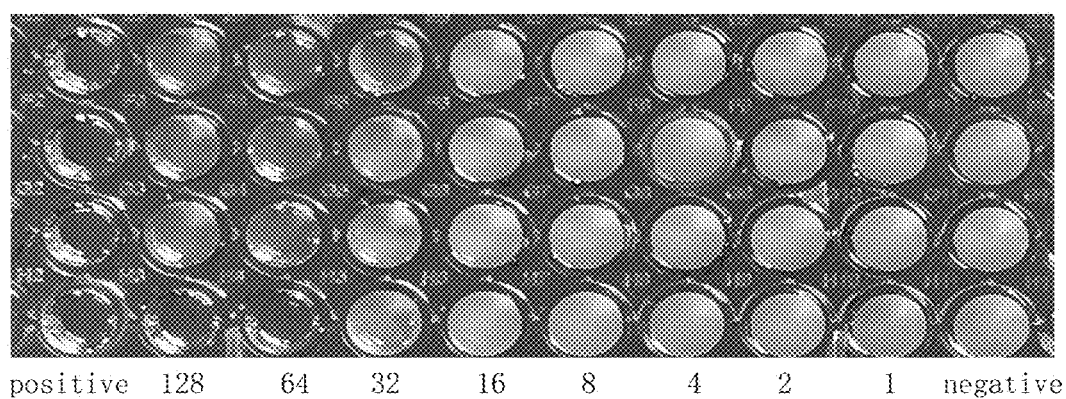
FIG. 2 shows the in vitro antibacterial activity of the pleuromulin rhein ester against drug-resistant bacteria MDR-PA 18-756.
Figure 3:
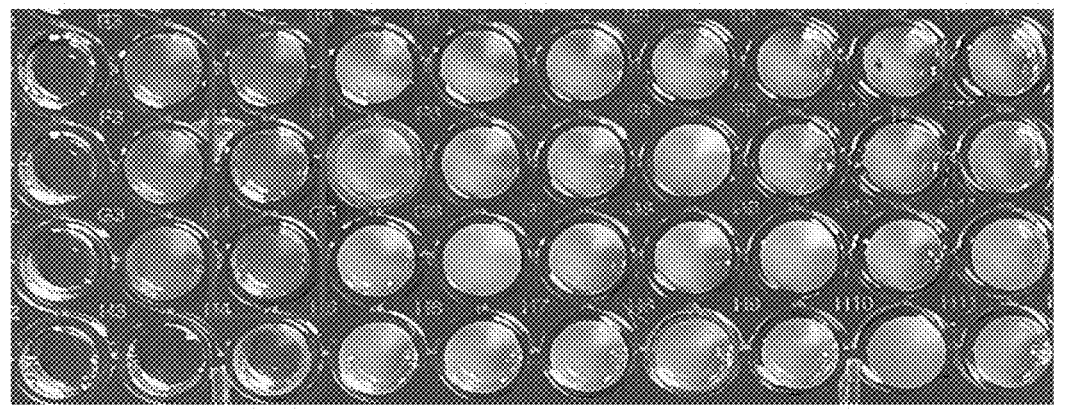
FIG. 3 shows the in vitro antibacterial activity of the pleuromulin rhein ester against drug-resistant bacteria MDR-PA 18-126.
Figure 4:
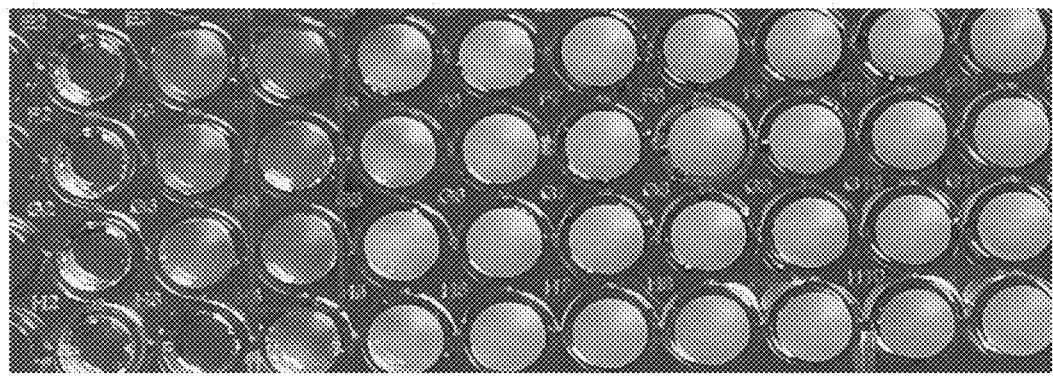
FIG. 4 shows the in vitro antibacterial activity of the pleuromulin rhein ester against drug-resistant bacteria CR-AB 18-184.
Figure 5:
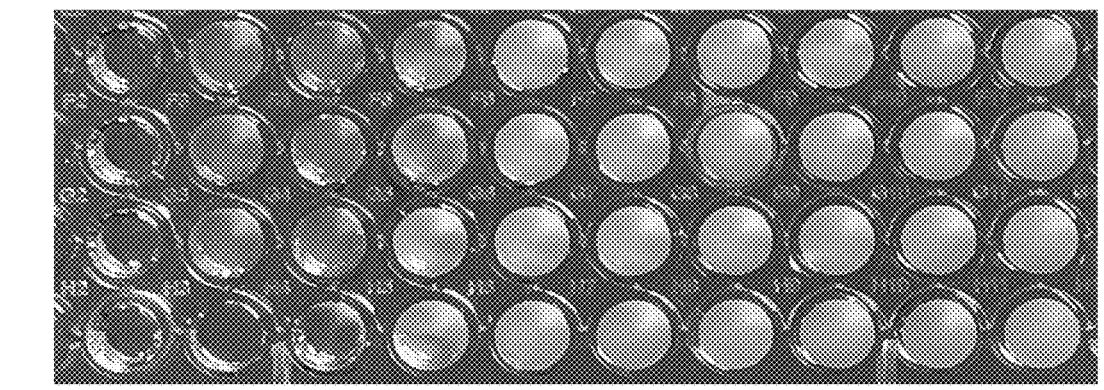
FIG. 5 shows the in vitro antibacterial activity of the pleuromulin rhein ester against drug-resistant bacteria CR-AB 18-560.

In FIGS. 1-5, the ten wells represent ten groups, from left to right, positive, 128 µg/mL, 64 µg/mL, 32 µg/mL, 16 µg/mL, 8 µg/mL, 4 µg/mL, 2 µg/mL, 1 µg/mL, Negative. FIG. 1 shows the in vitro antibacterial activity of pleuromulin rhein ester against drug-resistant bacteria MARS 18-575. FIG. 2 shows the in vitro antibacterial activity of pleuromulin rhein ester against drug-resistant bacteria MDR-PA 18-756. FIG. 3 shows the in vitro antibacterial activity of pleuromulin rhein ester against drug-resistant bacteria MDR-PA 18-126. FIG. 4 shows the in vitro antibacterial activity of pleuromulin rhein ester against drug-resistant bacteria CR-AB 18-184. FIG. 5 shows the in vitro antibacterial activity of pleuromulin rhein ester against drug-resistant bacteria CR-AB 18-560. The results are shown in Table 1.

TABLE 1

Minimum bacteriostatic concentration of test drug and positive drug (µg · mL$^{-1}$)

| | Strain | | | | |
|---|---|---|---|---|---|
| | MRSA | MDR-PA | | CR-AB | |
| Sample | 18-575 | 18-756 | 18-126 | 18-184 | 18-560 |
| Pleuromulin rhein ester | 64 | >128 | 64 | 64 | >128 |
| Ceftazidime | 128 | 128 | 128 | 128 | 128 |
| Vancomycin | 512 | \ | \ | \ | \ |
| Pleuromulin | >128 | >128 | >128 | >128 | >128 |
| Rhein | >128 | >128 | >128 | >128 | >128 |

According to the experimental results of FIG. 1-5 and Table 1, pleuromulin and rhein had no inhibitory effect on drug-resistant bacteria, while pleuromulin rhein ester showed a strong inhibitory effect on drug-resistant Gram-positive bacteria MRSA (MIC=64 µg/mL), drug-resistant Gram-positive bacteria MDR-PA (MIC=64 µg/mL) and CR-AB (MIC=64 µg/mL), and the bacteriostatic effect was stronger than that of positive control drugs. In summary, the pleuromulin rhein ester of the present invention can be used as antibacterial drug candidates for multidrug resistant *Pseudomonas aeruginosa*, carbapenem-resistant *Acinetobacter baumannii* and multidrug resistant *Staphylococcus aureus*, as well as further preclinical research.

What is claimed is:

1. A compound with anti-drug resistant bacteria activity having the following formula (I):

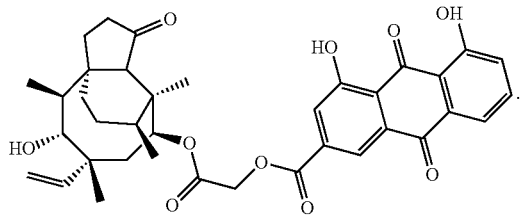

(I)

2. A method of preparing the compound of formula (I) of claim 1, comprising:

reacting a compound of formula (II) with a compound of formula (III) to obtain the compound of formula (I):

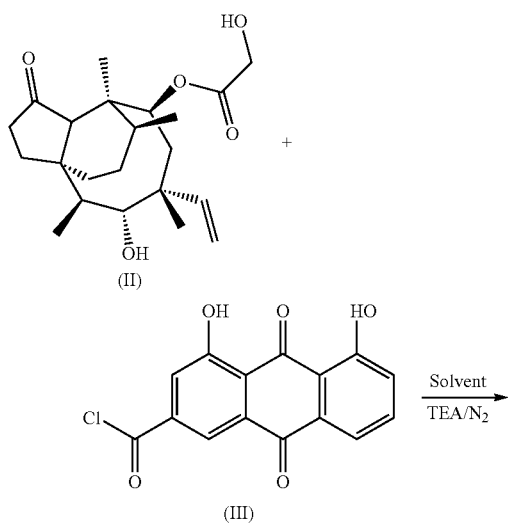

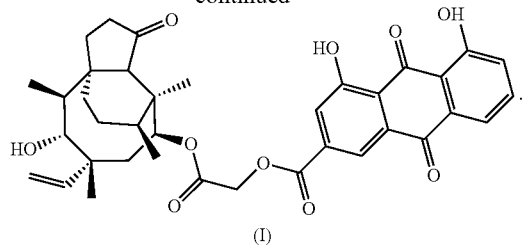

(I)

3. The method of claim 2, wherein the reaction of the compound of formula (II) with the compound of formula (III) comprises the following steps:
   placing the compound of formula (II) and the compound of formula (III), in a molar ratio of 1:1 to 1:1.3, in a reactor;
   adding an organic solvent and a catalytic amount of triethylamine under a nitrogen atmosphere to obtain a reaction mixture;
   heating the reaction mixture at 20-70° C. for 3-6 hours;
   extracting the concentrated solution with ethyl acetate to obtain a crude product; and
   purifying the crude product on a silica gel chromatography column with dichloromethane and ethyl acetate as an eluent to obtain the compound of formula (I).

4. The method of claim 3, wherein the organic solvent is selected from the group consisting of toluene, dichloromethane and N,N-Dimethylformamide.

5. The method of claim 4, wherein the organic solvent is dichloromethane.

6. The method of claim 3, wherein the molar ratio of the compound of formula (II) and the compound of formula (III) is 1:1.1.

7. The method of claim 3, wherein the reaction mixture is heated at 25° C.

8. The method of claim 3, wherein the reaction mixture is heated for 5 hours.

9. The method of claim 3, wherein the eluent is dichloromethane:ethyl acetate=2:1.

10. The compound of claim 1, wherein the compound is effective against multi-drug-resistant *Staphylococcus aureus*, multi-drug-resistant *Pseudomonas aeruginosa* and multi-drug-resistant *Acinetobacter baumannii*.

\* \* \* \* \*